United States Patent [19]
Almirante et al.

[11] Patent Number: 5,567,694
[45] Date of Patent: Oct. 22, 1996

[54] 17-ARYL AND 17-HETEROCYCLYL-5β,14β-ANDROSTANE DERIVATIVES ACTIVE ON THE CARDIOVASCULAR SYSTEM, PROCESSES FOR THEIR PREPARATION AND PHARMACEUTICAL COMPOSITIONS CONTAINING SAME

[75] Inventors: Nicoletta Almirante; Luigi Bernardi, both of Milan; Alberto Cerri, Gessate; Piero Melloni, Bresso; Gloria Padoani, Locate Triulzi; Luisa Quadri, Cernusco, all of Italy

[73] Assignee: SIGMA-TAU Industrie Farmaceutiche Riunite S.p.A., Rome, Italy

[21] Appl. No.: 128,114

[22] Filed: Sep. 29, 1993

[30] Foreign Application Priority Data

Sep. 29, 1992 [DE] Germany .................. 42 32 638.9

[51] Int. Cl.⁶ .................. A61K 31/56; A61K 31/58; C07D 207/00; C07J 1/00
[52] U.S. Cl. .................. 514/169; 514/172; 514/176; 552/612; 540/108
[58] Field of Search .................. 552/626, 612; 540/95, 108, 118; 514/176, 169, 172

[56] References Cited

U.S. PATENT DOCUMENTS 4,242,335  12/1980  Azadian et al. .................. 552/612

FOREIGN PATENT DOCUMENTS 0068596  3/1991  Japan .

OTHER PUBLICATIONS

Chemical Abstracts vol. 122: 31747 (1994).
Chemical Abstracts vol. 121:109398 (1994).
Grazyna Groszek et al., "Cardiotonic Steroids. Part 12.*) Practical Methods for an Introduction of a Hydroxyl Group into Position 14β of Androstane Skeleton", *Bull. Pol. Acad. Sci. Chem.*, vol. 314, No. 78, Mar. 19, 1986, pp. 313–320.

Naftali Danieli et al., "The 17α–Hydroxylation of Cardiac Aglycones, Conversion of the Cardenolide to the Cortisone Side–Chain", *Tetrahedron Letters*, No. 26, Sep. 27, 1962, pp. 1281–1285.
Francis G. Henderson et al., "Cardiac Glycosides and Aglycones by Synthesis and Microbiological Conversion", *J. Med. Chem.*, vol. 8, 1965, pp. 577–579.
Peter Leth Jorgensen, "Purification and Characterization of $(Na^+-K^+)$–ATPase III. Purification from the Outer Medulla of Mammalian Kidney after Selective Removal of Membrane Components by Sodium Dodecylsulphate", *Biochimica et Biophysica Acta*, vol. 356, 1974, pp. 36–51.
L. Brown et al., "Comparison of the Affinity of Human, Beef and Cat Hearth $(Na^+ + K^+)$–ATPase for Different Digitalis Derivatives", *Arzneim–Forsch./Drug Res.*, vol. 34(II), No. 10, 1984, pp. 1314–1318.
A. Doucet et al., "In vitro stimulation of Na–K–ATPase in rat thick ascending limb by dexamethasone", *Am. J. Physiol.*, vol. 251, 1986, pp. F851–F857.
G. Bianchi et al., "18. The Milan hypertensive strain", *Handbook of Hypertension*, vol. 4, 1984, pp. 328–349.

Primary Examiner—Mukund J. Shah
Assistant Examiner—Anthony Bottino
Attorney, Agent, or Firm—Oblon, Spivak, McClelland, Maier & Neustadt, P.C.

[57] ABSTRACT

17-aryl and heterocyclyl-5β,14β-androstane compounds having the formula (I)

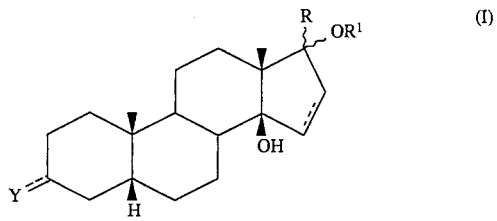

wherein R is an aryl ring or a saturated or unsaturated heterocyclic ring are active on the cardiovascular system and are useful in treating cardiovascular disorders.

8 Claims, No Drawings

17-ARYL AND 17-HETEROCYCLYL-5β,14β-ANDROSTANE DERIVATIVES ACTIVE ON THE CARDIOVASCULAR SYSTEM, PROCESSES FOR THEIR PREPARATION AND PHARMACEUTICAL COMPOSITIONS CONTAINING SAME

The present invention relates to 17-aryl and heterocyelyl-5β,14β-androstane derivatives, active on the cardiovascular system, to a process for their preparation and to pharmaceutical compositions containing same for the treatment of cardiovascular disorders such as heart failure and hypertension.

The invention relates to compounds of formula (I):

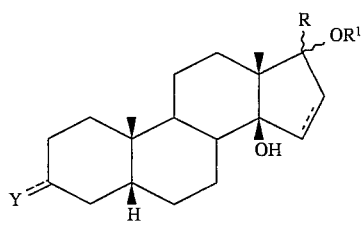

wherein:

the symbol ⁓ means that the substituents in position 17 can have an α or β configuration;

the symbol --- represents a single or a double bond;

Y is oxygen or guanidinoimino, when --- in position 3 is a double bond;

Y is hydroxy, $OR^2$ or $SR^2$, when --- in position 3 is a single bond and can have an α or β configuration;

R is an aryl ring or a saturated or unsaturated heterocyclic ring, containing one or more heteroatoms chosen from the group of oxygen, sulfur and nitrogen, unsubstituted or substituted by one or more halogen, hydroxy, hydroxymethyl, alkoxy, oxo, amino, alkylamino, dialkylamino, cyano, nitro, sulfonamido, C1-C6 lower alkyl group or $COR^3$, with the proviso that R is not 4-(2(5H)-oxo)-furyl or unsubstituted or substituted 3-furyl or 4-pyridazinyl rings;

$R^1$ is hydrogen; methyl; ethyl or n-propyl substituted by OH or $NR^4R^5$;

$R^2$ is hydrogen; methyl; C2-C6 alkyl or C3-C6 alkenyl or C2-C6 acyl, unsubstituted or substituted by a quaternary ammonium group or one or more $OR^6$, $NR7R^8$, CHO, $C(NH)NH_2$, guanidinoimino or by $NR^7R^8$ and hydroxy;

$R^3$ is hydrogen, hydroxy, C1-C4 alkoxy or C1-C4 alkyl;

$R^4$, $R^5$ are independently hydrogen; methyl; C2-C6 alkyl unsubstituted or substituted by $NR^9R^{10}$, or $R^4$ and $R^5$ taken together with the nitrogen atom form an unsubstituted or substituted saturated or unsaturated five- or six-membered heterocyclic ring optionally containing another heteroatom chosen from oxygen or sulfur or nitrogen;

$R^6$ is hydrogen; methyl; C2-C4 alkyl, unsubstituted or substituted by one or more $NR^9R^{10}$ or by $NR^9R^{10}$ and hydroxy;

$R^7$, $R^8$ are independently hydrogen; methyl; C2-C6 alkyl or C3-C6 alkenyl unsubstituted or substituted by one or more $NR^9R^{10}$, or $NR^9R^{10}$ and hydroxy, or $R^7$ and $R^8$ taken together with the nitrogen atom they are linked to, form an unsubstituted or substituted saturated or unsaturated five- or six-membered heterocyclic ring optionally containing another heteroatom chosen from oxygen or sulfur or nitrogen, or $R^7$ is hydrogen and $R^8$ is $C(NH)NH_2$;

$R^9$, $R^{10}$ are independently hydrogen, C1-C6 alkyl, or $R^9$ and $R^{10}$ taken together with the nitrogen atom they are linked to, form a saturated or unsaturated five- or six-membered monoheterocyclic ring.

The invention includes within its scope all the possible stereoisomers, in particular Z and E isomers, optical isomers and their mixtures and the metabolites and the metabolic precursors of the compounds of formula (I).

Also included in this invention are pharmaceutically acceptable salts of (I), which retain the biological activity of the base and are derived from such known pharmacologically acceptable acids such as e.g. hydrochloric, sulfuric, phosphoric, malic, tartaric, maleic, citric, methanesulfonic or benzoic acid.

When R is an aryl ring it is preferably phenyl or naphthyl unsubstituted or substituted preferably by methyl, ethyl, isopropyl, methoxy, halide, cyano, nitro, sulfonamido, amino, dimethylamino, carboxy, dicarboxy, di(methoxycarbonyl), di(hydroxymethyl).

When R is a saturated or unsaturated heterocyclic ring it is preferably 1,3-dithian-2-yl, 2-furyl, tetrahydrofuryl, thienyl, pyrrolyl, pyridyl, pyridyl-N-oxide, pyrimidinyl, pyridazinyl, piperidyl, pyrazolyl, imidazolyl, methylimidazolyl, imidazolinyl, thiazolyl, oxazolyl, oxazolinyl, isoxazolyl, triazolyl, 2-oxo-(1H)-pyridyl, 2-oxo-(2H)-5-pyranyl, 2-oxo-(SH)-4-pyrrolyl ring.

The alkyl and alkenyl groups may be branched or straight chain groups.

The C1-C6 alkyl group is preferably a C1-C4 alkyl group, e.g. methyl, ethyl, n-propyl, iso-propyl, n-butyl, sec-butyl.

The C2-C6 alkyl group is preferably a C2-C4 alkyl group, e.g. ethyl, n-propyl,/so-propyl, n-butyl, sec-butyl.

The C3-C6 alkenyl group is preferably a C3-C4 alkenyl group, e.g. 2-propenyl, 2-butenyl.

The C2-C6 acyl is preferably a C2-C4 acyl group, e.g. acetyl, propionyl, butyryl.

The quaternary ammonium group is preferably a trimethylammonium- or a N-methylpyrrolidinium- or a N-methylpiperidinium-group.

The $R^1$ group is preferably hydrogen, 2-aminoethyl, 3-aminopropyl, 2-(1-pyrrolidinyl)ethyl, 3-(1-pyrrolidinyl)propyl, 2-hydroxyethyl or 3-hydroxypropyl.

The $OR^6$ group is preferably hydroxy, 2-aminoethoxy, 3-aminopropoxy, 2-dimethylaminoethoxy, 3-dimethylaminopropoxy, 3-amino-2-hydroxypropoxy, 2,3-diaminopropoxy, 2-(1-pyrrolidinyl)ethoxy, 3-(1-pyrrolidinyl)propoxy.

The $NR^7R^8$ group is preferably amino, methylamino, ethylamino, n-propylamino, dimethylamino, diethylamino, pyrrolidinyl, morpholino, piperazinyl, 1-imidazolyl, 2-aminoethylamino, 3-aminopropylamino.

Preferred examples of specific compounds according to the present invention are

17β-Phenyl-5β-androst-15-ene-3β,14β,17α-triol

3β-(2-(1-Pyrrolidinyl)ethoxy)-17β-phenyl-5β-androst-15-ene-14β,17α-diol

17β-Phenyl-5β-androstane-3β,14β,17α-triol

3β-(2-(1-Pyrrolidinyl)ethoxy)-17β-phenyl-5β-androstane-14β,17α-diol

17β-Phenyl-17α-(2-(1-pyrrolidinyl)ethoxy)-5β-androstane-3β,14β-diol

3β,17α-Bis(2-(1-pyrrolidinyl)ethoxy)-17β-phenyl-5β-androstane-14β-ol

17β-(2-Methoxyphenyl)-5β-androstane-3β,14β,17α-triol

3β-(2-(1-Pyrrolidinyl)ethoxy)-17β-(2-methoxyphenyl)-5β-androstane-14β,17α-diol

17β-(2-Methoxyphenyl)-17α-(2-(1-pyrrolidinyl)ethoxy)-5β-androstane-3β,14β-diol

3β,17α-Bis(2-(1-pyrrolidinyl)ethoxy)-17β-(2-methoxyphenyl)-5β-androstane-14β-ol

17β-(3-Methoxyphenyl)-5β-androstane-3β,14β,17α-triol

3β-(2-(1-Pyrrolidinyl)ethoxy)-17β-(3-methoxyphenyl)-5β-androstane-14β,17α-diol

17β-(3-Methoxyphenyl)-17α-(2-(1-pyrrolidinyl)ethoxy)-5β-androstane-3β,14β-diol
3β,17α-Bis(2-(1-pyrrolidinyl)ethoxy)-17β-(3-methoxyphenyl)-5β-androstane-14β-ol
17β-(4-Methoxyphenyl)-5β-androst-15-ene-3β,14β,17α-triol
3β-(2-(1-Pyrrolidinyl)ethoxy)-17β-(4-methoxyphenyl)-5β-androst-15-ene-14β,17α-diol
17β2-(4-Methoxyphenyl)-5β-androstane-3β,14β,17α-triol
3β-(2-(1-Pyrrolidinyl)ethoxy)-17β-(4-methoxyphenyl)-5β-androstane-14β,17α-diol
17β-(4-Methoxyphenyl)-17α-(2-(1-pyrrolidinyl)ethoxy)-5β-androstane-3β,14β-diol
3β,17α-Bis(2-(1-pyrrolidinyl)ethoxy)-17β-(4-methoxyphenyl)-5β-androstane-14β-ol
17β-(3-Hydroxyphenyl)-5β-androstane-3β,14β,17α-triol
17β-(4-Hydroxyphenyl)-5β-androstane-3β,14β,17α-triol
17β-(4-Methylphenyl)-5β-androstane-3β,14β,17α-triol
3β-(2-(1-Pyrrolidinyl)ethoxy)-17β-(4-methylphenyl)-5β-androstane-14β,17α-diol
17β-(4-Methylphenyl)-17α-(2-(1-pyrrolidinyl)ethoxy)-5β-androstane-3β,14β-diol
3β,17α-Bis(2-(1-pyrrolidinyl)ethoxy)-17β-(4-methylphenyl)-5β-androstane-14β-ol
17β-(4-Chlorophenyl)-5β-androstane-3β,14β,17α-triol
3β-(2-(1-Pyrrolidinyl)ethoxy)-17β-(4-chlorophenyl)-5β-androstane-14β,17α-diol
17β-(4-Chlorophenyl)-17α-(2-(1-pyrrolidinyl)ethoxy)-5β-androstane-3β,14β-diol
3β,17α-Bis(2-(1-pyrrolidinyl)ethoxy)-17β-(4-chlorophenyl)-5β-androstane-14β-ol
17β-(4-Cyanophenyl)-5β-androstane-3β,14β,17α-triol
17β-(2-Nitrophenyl)-5β-androstane-3β,14β,17α-triol
17β-(4-Dimethylaminophenyl)-5β-androstane-3β,14β,17α-triol
17β-(4-Carboxyphenyl)-5β-androstane-3β,14β,17α-triol
17β-(2-Furyl)-5β-androstane-3β,14β,17α-triol
3β-(2-(1-Pyrrolidinyl)ethoxy)-17β-(2-furyl)-5β-androstane-14β,17α-diol
17β-(2-Furyl)-17α-(2-(1-pyrrolidinyl)ethoxy)-5β-androstane-3β,14β-diol
3β,17α-Bis(2-(1-pyrrolidinyl)ethoxy)-17β-(2-furyl)-5β-androstane-14β-ol
17β-(3-Thienyl)-5β-androstane-3β,14β,17α-triol
3β-(2-(1-Pyrrolidinyl)ethoxy)-17β-(3-thienyl)-5β-androstane-14β,17α-diol
17β-(3-Thienyl)-17α-(2-(1-pyrrolidinyl)ethoxy)-5β-androstane-3β,14β-diol
3β,17α-Bis(2-(1-pyrrolidinyl)ethoxy)-17β-(3-thienyl)-5β-androstane-14β-ol
17β-(2-Pyridyl)-5β-androstane-3β,14β,17α-triol
17β-(3-Pyridyl)-5β-androstane-3β,14β,17α-triol
17β-(4-Pyridyl)-5β-androstane-3β,14β,17α-triol
17β-(2-Pyridyl-N-oxide)-5β-androstane-3β,14β,17α-triol
17β-(3-Pyridyl-N-oxide)-5β-androstane-3β,14β,17α-triol
17β-(4-Pyridyl-N-oxide)-5β-androstane-3β,14β,17α-triol
17β-(2-Oxo-(1H)-4-pyridyl)-5β-androstane-3β,14β,17α-triol
17β-(2-Oxo-(1H)-5-pyridyl)-5β-androstane-3β,14β,17α-triol
17β-(2-Oxo-(2H)-5-pyranyl)-5β-androstane-3β,14β,17α-triol
17β-(2-Piperidyl)-5β-androstane-3β,14β,17α-triol
17β-(2-Pyrimidinyl)-5β-androstane-3β,14β,17α-triol
17β-(4-Pyrimidinyl)-5β-androstane-3β,14β,17α-triol
17β-(2-Imidazolyl)-5β-androstane-3β,14β,17α-triol
17β-(2-(1-Methyl)imidazolyl)-5β-androstane-3β,14β,17α-triol
17β-(1,2-Dimethyl-5-imidazolyl)-5β-androstane-3β,14β,17α-triol
17β-(2-Thiazolyl)-5β-androstane-3β,14β,17α-triol
17β-(5-Thiazolyl)-5β-androstane-3β,14β,17α-triol
17β-(4-Isoxazolyl)-5β-androstane-3β,14β,17α-triol and the corresponding 3β-(2-hydroxyethoxy), 3β-(3-hydroxypropoxy), 3β-(2,3-dihydroxypropoxy), 3β-(2-aminoethoxy), 3β-(3-aminopropoxy), 3β-(2-methylaminoethoxy), 3β-(3-methylaminopropoxy), 3β-(2-dimethylaminoethoxy), 3β-(3-dimethylaminopropoxy), 3β-(2-diethylaminoethoxy), 3β-(3-diethylaminopropoxy), 3β-(3-(1-pyrrolidinyl)propoxy), 3β-(2,3-diaminopropoxy), 3β-(2-(2-(1-pyrrolidinyl)ethoxy)ethoxy), 3β-(2-guanidinoethoxy), 3β-(3-guanidinopropoxy) of the 3β-(2-(1-pyrrolidinyl)ethoxy) derivatives;

and the corresponding 17α-(2-hydroxyethoxy), 17α-(3-hydroxypropoxy), 17α-(2-aminoethoxy), 17α-(3-aminopropoxy), 17α-(3-(1-pyrrolidinyl)propoxy) of the 17α-(2-(1-pyrrolidinyl)ethoxy) derivatives;

and the corresponding 3-oxo and 3-guanidinoimino of the corresponding 3β-ol derivatives;

and the corresponding 3β,17α-bis-(2-hydroxyethoxy), 3β,17α-bis-(3-hydroxypropoxy), 3β,17α-bis-(2,3-dihydroxypropoxy), 3β,17α-bis-(2-aminoethoxy), 3β,17α-bis-(3-aminopropoxy) of the corresponding 3β,17α-bis(2-(1-pyrrolidinyl)ethoxy) derivatives;

and the corresponding 3β-(2-aminoethylthio), 3β-(3-aminopropylthio), 3β-(2-(1-pyrrolidinyl)ethylthio), 3β-(3-(1-pyrrolidinyl)propylthio), 3β-(2-(2-(1-pyrrolidinyl)ethoxy)ethylthio) of the 3β-(2-(1-pyrrolidinyl)ethoxy) derivatives.

The invention furthermore provides a process for the preparation of compounds of general formula (I), wherein --- is a single or double bond, wherein Y, R and R¹ are as above defined, which comprises reacting aryl or heterocyclyl organometallics with compounds of formula (II)

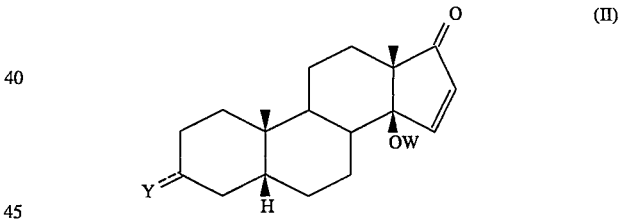

wherein --- is a single or double bond, wherein W is hydrogen or a protective group, Y is as above defined, with the proviso that Y is not a guanidinoimino and do not contain a guanidinoimino or a guanidino or an amidino group, the hydroxy, mercapto, amino and oxo groups if any present in Y being protected, if necessary, with known methods, to give, if necessary, after removal of protective groups, if any, present in Y and/or W, a compound of general formula (I), which can be converted into another compound of general formula (I), by known methods such as conversion of hydroxy into mercapto function, alkylation of hydroxy or mercapto groups, oxydation of hydroxy or reduction of oxo functions, formation of guanidinoimino or guanidino or amidino groups from oxo or primary amino or cyano groups respectively, or reduction of a double bond to a single bond.

The nucleophilic reactions of aryl or heterocyclyl organometallics, wherein the metal is lithium, magnesium, cerium, zirconium or titanium, with compounds of formula (II) are carried out in an inert aprotic solvent, such as for example tetrahydrofuran, diethyl ether, dioxane, benzene, cyclohexane, or a mixture of said solvents at a temperature ranging from −78° C. to room temperature.

Examples of conversions of compounds of general formula (I) into other compounds of formula (I) are the following.

Compounds (I) wherein the 15–16 bond is a single bond can be obtained by selective hydrogenation of the compounds (I), wherein the 15–16 bond is a double bond, with e.g. hydrogen using palladium or platinum oxide as catalysts.

Compounds (I) wherein an oxo function is present can be obtained by oxidation of the corresponding compounds (I) with a hydroxy function with e.g. $CrO_3$ in pyridine or tetrapropylammonium perruthenate and N-methylmorpholine-N-oxide in methylene chloride, at temperature ranging from 0° C. to room temperature.

Compounds (I) wherein Y is an α-hydroxy group can be obtained by reduction of the corresponding compounds (I) wherein Y is oxygen with complex hydrides, e.g. $NaBH_4$, $LiAlH_4$ or lithium tri-tert-butoxyalumihum hydride in methanol, tetrahydrofuran or diethyl ether, at temperature ranging from −78° C. to room temperature.

Compounds (I) wherein a guanidinoimino group is present can be obtained by condensation of the corresponding compounds (I) wherein an aldehydic or ketonic oxo function is present with e.g. aminoguanidine hydrogencarbonate in ethanol, methanol, acetonitrile, dioxane, tetrahydrofuran, water or a mixture of the said solvents at temperature ranging from room temperature to the solvent reflux temperature.

Compounds (I) wherein Y is a β-mercapto group can be obtained by ammonolysis of the 3β-acetylthio derivatives (I) that are in turn obtained by reaction of the corresponding 3α-hydroxy derivatives (I) with e.g. thiolacetic acid in the presence of a dialkyl azodicarboxylate and triphenylphosphine, at temperature ranging from 0° C. to room temperature.

Compounds (I) wherein an ethereal or thioethereal function is present, e.g. wherein Y is $OR^2$ or $SR^2$ and wherein $R^1$ and/or $R^2$ are different from hydrogen, can be obtained from the corresponding compounds of formula (I), wherein Y is $OR^2$ or $SR^2$ and $R^1$ and/or $R^2$ are hydrogen, by reaction with alkylating compounds of formula (III) or (IV)

$R^1$—Z      (III)

$R^2$—Z      (IV)

wherein $R^1$ and $R^2$ are as above defined with the proviso that they are different from hydrogen and Z is an electron-withdrawing group, such as halogen, mesyloxy, or tosyloxy group. The reaction is carried out in an inert aprotic solvent, such as tetrahydrofuran, dioxane, dimethylformamide, dimethylsulfoxyde or in the neat $R^1$-Z and $R^2$-Z in the presence of a base, e.g. sodium or potassium hydride, at a temperature ranging from 0° C. to reflux temperature of the reaction mixture.

Compounds (I) wherein a C(=NH)$NH_2$ is present can be obtained by reacting the corresponding compounds of formula (I) wherein a CN group is present with e.g. methylchloroaluminum amide.

Compounds (I)wherein a guanidino group is present can be obtained by reacting the corresponding compounds of formula wherein a primary amine is present with e.g. 1-amidino-3,5-dimethylpyrazole nitrate.

All said transformations are examples of well established procedures described in Organic Chemistry (see for example: J. March "Advanced Organic Chemistry", J. Wiley & Sons, 1985; D. Barton and W. D. Oilis "Comprehensive Organic Chemistry", Pergamon Press, 1979) well known to those skilled in the art.

Compound of formula (II) wherein Y is 3β-hydroxy and W is hydrogen is a known compound (G. Groszek et al., Bull. Pol. Acad. Sci., Chem., 34, 1986, 313).

Compounds of formula (II) wherein Y has the other meanings are obtained from the corresponding 3β-hydroxy (II) by conversion of hydroxy into mercapto function, alkylation of hydroxy or mercapto groups, oxydation of hydroxy or reduction of oxo functions with methods well known to those skilled in the art and described above.

Compounds of general formula (III) and (IV) are known compounds, generally commercially available or preparable from known compounds by known methods.

Compound 3β,14β,17α-trihydroxy-5β-card-20(22)-enolide (Ref. comp.) is known (N. Danieli, et al., Tetrah. Lett., 1962, 1281); this compound and its congeners are described as agents against cardiac insufficiency (DT Pat. 2614-046; F. G. Henderson and K. K. Chen, J. Med. Chem., 1965, 577), but do not show antihypertensive action.

We have found that the derivatives (I), prepared according to the invention, and their pharmaceutically acceptable salts have much reduced toxicity compared to the known 3β,14β, 17α-trihydroxy-5β-card-20(22)-enolide and are useful agents for the treatment of cardiovascular disorders, such as heart failure and hypertension.

Moreover said compounds (I) show affinity for the receptor site of the $Na^+,K^+$-ATPase and behave as partial agonists on the enzymatic activity of the $Na^+,K^+$-ATPase.

To test the affinity for the receptor site of the $Na^+,K^+$-ATPase and the inhibitory activity on the enzyme, the following tests were used:

a) displacement of the specific $^3$H-ouabain binding from the $Na^+,K^+$-ATPase receptor purified according to Jorghensen (Jorghensen P., BBA, 1974, 356, 36) and Erdmann ( Erdmann E. et al., Arzneim. Forsh., 1984, 34, 13 14);

b) inhibition of the activity of the purified $Na^+,K^+$-ATPase measured as % of hydrolysis of $^{32}$P-ATP in presence and in absence of the tested compound (Doucet A. et al., Am. J. Physiol, 1986, 251, F851).

The ability of these compounds to lower blood pressure was tested by using animal models with genetic arterial hypertension, in particular, spontaneous hypertensive rats of the Milan (MHS) (Bianchi G., Ferrari P., Barber B., The Milan Hypertensive strain. In Handbook of hypertension. Vol.4: Experimental and genetic models of hypertension. Ed. W. de jong-Elsevier Science Publishers B.V.,1984: 328–349).

The procedure adopted to test the antihypertensive activity of the compounds on the above mentioned model was the following:

systolic blood pressure (SBP) and heart rate (HR) were measured by an indirect tail-cuff method in three-month old hypertensive rats (MHS) before beginning the treatment (basal values). The rats were then subdivided in two groups of at least 7 animals each, one receiving the compound the other, the control group, receiving only the vehicle. The compound, suspended in METHOCEL 0.5% (w/v), was administered daily by mouth, for ten days. SBP and HR were measured daily 6 and 24 hours after the treatment. At the end of the ten day treatment period, a washout period of at least two days was carried out, in order to check for how long the SBP was mantained low or the basal values were re-established.

The affinity and the inhibitory activity of some compounds and of the Ref. compound. in the two tests are shown in the following table:

|  | Binding ³H-Ouab. Displacement -log IC50 | Inhibitory Activity -log IC50 |
| --- | --- | --- |
| Comp. I-ac | 5.4 | 4.1 |
| Comp. I-ad | 5.2 | 4.0 |
| Comp. I-ae | 5.9 | 4.7 |
| Comp. I-ag | 5.9 | 4.6 |
| Comp. I-ai | 5.0 | 4.1 |
| Comp. I-al | 5.8 | 4.8 |
| Comp. I-am | 5.9 | 4.8 |
| Comp. I-an | 5.8 | 4.6 |
| Comp. I-ao | 5.5 | 4.2 |
| Comp. I-ap | 5.8 | 4.6 |
| Comp. I-aq | 5.3 | 4.3 |
| Comp. I-ar | 5.8 | 4.6 |
| Comp. I-at | 5.0 | 4.0 |
| Comp. I-au | 5.6 | 4.5 |
| Comp. I-av | 6.0 | 4.8 |
| Comp. I-ay | 5.6 | 4.5 |
| Comp. I-az | 5.4 | 4.4 |
| Comp. 1-ba | 5.7 | 4.5 |
| Comp. 1-bb | 5.4 | 4.3 |
| Comp. I-bc | 5.6 | 4.6 |
| Comp. I-bd | 5.3 | 4.3 |
| Comp. I-be | 5.4 | 4.3 |
| Comp. I-bf | 5.7 | 4.6 |
| Comp. I-bg | 5.6 | 4.6 |
| Comp. I-bk | 5.7 | 4.7 |
| Comp. I-bj | 5.7 | 4.6 |
| Ref. comp. | 5.9 | 5.3 |

The activity of the Ref. compound and some new compound in lowering blood pressure in spontaneous hypertensive MHS rats is shown in the following table:

| SYSTOLIC BLOOD PRESSURE FALL IN SPONTANEOUS HYPERTENSIVE RATS (MHS) | | | | |
| --- | --- | --- | --- | --- |
| COMPOUND | RATS | DOSE* mg/Kg/os | SBP mm Hg | HR beats/min. |
| Controls | 7 | METHOCEL | 172 +/− 2.0 | 328 +/− 8.6 |
| Comp. I-ac | 7 | 20 | 160 +/− 4.5 | 331 +/− 8.5 |
| Comp. I-ag | 7 | 20 | 157 +/− 4.2 | 330 +/− 9.8 |
| Comp. I-au | 7 | 20 | 156 +/− 4.1 | 335 +/− 10.5 |
| Comp. 1-bb | 7 | 20 | 154 +/− 3.0 | 339 +/− 6.8 |
| Ref. comp. | 7 | 20 | 174 +/− 2.1 | 340 +/− 10.2 |

*in METHOCEL 0.5% w/v

The following examples illustrate the invention without limiting it.

EXAMPLE 1

17β-Phenyl-5β-androst-15-ene-3β,14β,17α-triol (I-aa)

11.09 g of anhydrous CeCl₃ were suspended in dry tetrahydrofuran (14 ml), under nitrogen, the suspension was cooled to −78° C. for half an hr, then 22.20 ml of phenyllithium (solution 2M in cyclohexane-ether) were added. After being kept at the same temperature for 2 hrs, 4.50 g of 3β,14β-dihydroxy-5β-androst-15-en-17-one (G. Groszek et al., *Bull. Pol. Acad. Sci., Chem.*, 34, 1986, 313) were added to the mixture; after an hr the reaction mixture was diluted with 150 ml of water, filtered through celite, and extracted with ethyl acetate; the combined extracts were dried over anhydrous sodium sulfate and evaporated to dryness under reduced pressure. The crude product was purified by flash-chromatography (SiO₂) using ethyl acetate/cyclohexane 70/30 as eluant to give 4.20 g of the title compound (I-aa) as a white solid.

¹H-NMR (300 MHz, DMSO-d₆, ppm from TMS): 0.55 (3H, s); 0.82 (3H, s); 3.50 (1H, s); 3.90 (1H, m); 4.21 (1H, d); 4.90 (1H, s); 5.78 (1H, d); 6.20 (1H, d); 7.10–7.20 (3H, m); 7.41 (2H, d).

EXAMPLE 2

3β-(2-(1-Pyrrolidinyl)ethoxy)-17β-phenyl-5β-androst-15-ene-14β,17α-diol (I-ab)

To a suspension of 0.080 g of NaH (60% dispersion in mineral oil) in 8 ml of dry tetrahydrofuran, 0.28 g of 17β-phenyl-5β-androst-15-ene-3β,14β,17α-triol (I-aa) were added at room temperature, under nitrogen. The mixture was refluxed for 3 hrs, then 0.67 g of 1-(2-chloroethyl)pyrrolidine were added; the suspension was refluxed for 2 hrs; 10 ml of water were added cautiously and the tetrahydrofuran was distilled at reduced pressure. The residue was extracted with methylene chloride, the organic layer was dried over anhydrous sodium sulfate and evaporated to dryness, under reduced pressure. The crude product was purified by flash-chromatography (SiO₂) using methylene chloride/methanol 90/10 as eluant to give 0.050 g of the title compound (I-ab), as a white solid.

¹H-NMR (300 MHz, DMSO-d₆, ppm from TMS): 0.56 (3H, s); 0.83 (3H, s); 2.44 (4H, m); 2.52 (2H, t); 3.38 (2H, m); 3.48 (1H, s); 3.54 (1H, m); 4.93 (1H, s); 5.78 (1H, d); 6.20 (1H, d); 7.11–7.20 (3H, m);. 7.41 (2H, d).

EXAMPLE 3

17β-Phenyl-5β-androstane-3β,14β,17α-triol (I-ac)

To a solution of 4.0 g of 17β-phenyl-5β-androst-15-ene-3β,14β,17α-triol in 300 ml of ethyl acetate, 0.40 g of PtO₂ were added. The resulting mixture was shaken with H₂ at room temperature. After half an hr the resulting mixture was filtered over celite and evaporated to give 3.8 g of the title compound (I-ac) as a white solid.

¹H-NMR (300 MHz, CDCl₃, ppm from TMS): 0.70 (3H, s); 0.95 (3H, s); 2.71 (1H, m): 4.15 (1H, m); 7.20–7.40 (3H, m); 7.61 (2H, d).

EXAMPLE 4

3β-(2-Hydroxyethoxy)-17β-phenyl-5β-androstane-14β,17α-diol (I-ad)

To a suspension of 1.1 g of NaH (60% dispersion in mineral oil) in 110 ml of dry tetrahydrofuran, 3.5 g of 17β-phenyl-5β-androstane-3β,14β,17α-triol (I-ac) were added at room temperature, under nitrogen and the resulting mixture was refluxed for 3 hr; 5.5 ml of bromoacetaldehyde diethylacetal were added and the suspension was kept at reflux temperature for half an hr, then 30 ml of water were added cautiously, and the tetrahydrofuran was distilled under reduced pressure. The residue was extracted with methylene chloride, the organic layer was dried over anhydrous sodium sulfate and evaporated to dryness under reduced pressure. The crude product was purified by flash-chromatography (SiO₂) using n-hexane/ethyl acetate 80/20 as eluant to give 1.60 g of 3β-(2,2-diethoxyethoxy)-17β-phenyl-5β-androstane- 14β,17α-diol as a dense oil.

¹H-NMR (300 MHz, CDCl₃, ppm from TMS): 0.71 (3H, s); 0.95 (3H, s); 2.70 (1H, m); 3.45 (2H, d); 3.53–3.70 (5H, m); 4.60 (1H, m); 7.20–7.40 (3H, m); 7.61 (2H, d).

A solution of 1.50 g of 3β-(2,2-diethoxyethoxy)-17β-phenyl-5β-androstane-14β,17α-diol in 120 ml of dioxane and 90 ml of a saturated solution of tartaric acid was heated at 60° C. for 2 hrs in a nitrogen; 50 ml of water were then added and the residue was extracted with methylene chloride. The organic layer was washed with water, dried over anhydrous sodium sulfate and evaporated to dryness under reduced pressure. The crude product was purified by flash-chromatography ($SiO_2$) using n-hexane/ethyl acetate 70/30 as eluant to give 0.95 g of 3β-formylmethoxy-17β-phenyl-5β-androstane-14β,17α-diol as a white solid.

$^1$H-NMR (300 MHz, $CDCl_3$, ppm from TMS): 0.71 (3H, s); 0.95 (3H, s); 2.71 (1H, m); 3.70 (1H, m); 4.00 (2H, s); 7.20–7.40 (3H, m); 7.60 (2H, d); 9.75 (1H, s).

To a solution of 0.95 g of 3β-formylmethoxy-17β-phenyl-5β-androstane-14β,17α-diol in 50 ml of methanol, 0.165 g of sodium borohydride were added slowly at 0° C.; after half an hr the temperature of the mixture was left to rise to 25° C. After 2 hrs 10 ml of water were added, the methanol was distilled under reduced pressure, and the mixture was extracted with methylene chloride; the organic layer was washed with water, dried over anhydrous sodium sulfate and evaporated to dryness under reduced pressure. The crude product was purified by flash-chromatography ($SiO_2$) using n-hexane/ethyl acetate 80/20 as eluant to give 0.85 g of the title compound (I-ad) as a white solid.

$^1$H-NMR (300 MHz, $CD_3OD$, ppm from TMS): 0.73 (3H, s); 0.98 (3H, s): 2.09 (1H, m); 2.25 (1H, m); 2.45 (1H, m): 3.52 (2H, m): 3.68 (3H, m); 7.20–7.40 (3H, m); 7.60 (2H, d).

EXAMPLE 5

3β-(3-Dimethylaminopropoxy)-17β-phenyl-5β-androstane-14β,17α-diol (I-ae)

The title compound (I-ae) (0.25 g) was obtained as a white solid from 17β-phenyl-5β-androstane-3β,14β,17α-triol (I-ac)(0.65 g)and 3-chloro-N,N-dimethylaminopropane using the same procedure described in Ex. 2.

$^1$H-NMR (300 MHz, $CDCl_3$, ppm from TMS): 0.71 (3H, s); 0.95 (3H, s); 2.52–2.75 (7H, m); 3.48–3.59 (2H, m); 3.63 (1H, m); 7.20–7.40 (3H, m); 7.62 (2H, d).

EXAMPLE 6

3β-(3-Hydroxypropoxy)-17β-phenyl-5β-androstane-14β,17α-diol (I-af)

To a suspension of 0.25 g of NaH (60% dispersion in mineral oil) in 25 ml of dry tetrahydrofuran 0.80 g of 17β-phenyl-5β-androstane-3β,14β,17α-triol (I-ac) were added at room temperature, under nitrogen and the resulting mixture was refluxed for 2 hr; 0.8 g of allyl bromide were added and the reflux continued for half an hr. The mixture was quenched with water and the organic solvent was distilled under reduced pressure. The residue was extracted with ethyl acetate, the organic solution was dried over anhydrous sodium sulfate and evaporated to dryness under reduced pressure. The residue was purified by flash-chromatography ($SiO_2$) using n-hexane/ethyl acetate 80/20 as eluant to give 0.45 g of 3β-(prop-2-enoxy)-17β-phenyl-5β-androstane- 14β,17α-diol as a dense oil.

$^1$H-NMR (300 MHz, $CDCl_3$, ppm from TMS): 0.71 (3H, s); 0.95 (3H, s); 2.7 (1H, m); 3.67 (1H, m); 3.90–4.00 (2H, M); 5.13–5.20 (1H, m); 5.23–5.32 (1H, m); 5.86–6.02 (1H, m); 7.20–7.40 (3H, m); 7.60 (2H, d).

To a solution of 0.136 g of 9-borabicyclo[3.3.1]nonane in 300 ml of dry tetrahydrofuran, 0.4 g of 3β-(prop-2-enoxy)-17β-phenyl-5β-androstane-14β,17α-diol in 10 ml of tetrahydrofuran were added under nitrogen, at room temperature. The solution was stirred for 6 hrs, then 0.6 ml of ethanol, 0.2 ml of sodium hydroxide 6N and 0.4 ml of hydrogen peroxide 30% were added. The mixture was stirred at 50° C. for one hr, quenched with a solution of 0.6 g of potassium carbonate in 16 ml of water and the organic solvent distilled under reduced pressure. The residue was extracted with methylene chloride, the organic solution was dried over anhydrous sodium sulfate and evaporated to dryness under reduced pressure. The residue was purified by flash-chromatography ($SiO_2$) using n-hexane/ethyl acetate 70/30 as eluant to give 0.3 g of the title compound (I-af) as a white amorphous solid.

$^1$H-NMR (300 MHz, $CDCl_3$, ppm from TMS): 0.71 (3H, s); 0.95 (3H, s); 2.70 (1H, m); 3.57–3.68 (3H, m); 3.91–3.99 (2H, m); 7.20–7.40 (3H, m); 7.60 (2H, d).

EXAMPLE 7

3β-(3-Aminopropoxy)-17β-phenyl-5β-androstane-14β,17α-diol (I-ag)

A solution of 0.082 ml of diethyl azodicarboxylate was added dropwise, under nitrogen, to a solution of 0.22 g of 3β-(3-hydroxypropoxy)-17 β-phenyl-5β-androstane-14β,17α-diol (I-af), 0.075 g of phthalimide and 0.13 g of triphenylphosphine in 2 ml of tetrahydrofuran at room temperature. After 2 hrs the solvent was removed under reduced pressure and the crude product was purified by flash-chromatography ($SiO_2$) using n-hexane/ethyl acetate 80/20 to give 0.20 g of 3β-(3-phthalimidopropoxy)-17β-phenyl-5β-androstane-14β,17α-diol as a white solid.

$^1$H-NMR (300 MHz, $CDCl_3$, ppm from TMS): 0.71 (3H, s); 0.95 (3H, s); 2.70 (1H, m); 3.38–3.50 (2H, m); 3.55 (1H, m); 3.83 (2H, t); 7.20–7.40 (3H, m); 7.60 (2H, d); 7.71–7.77 (2H, m); 7.83–7.94 (2H, m).

To a solution of 0.20 g of 3β-(3-phthalimidopropoxy)-17β-phenyl-5β-androstane- 14β,17α-diol in 25 ml of ethanol (96%) 0.083 g of hydrazine hydrate were added at room temperature. The mixture was kept at reflux temperature for 4 hrs, then 5 ml of water were added and the ethanol distilled under reduced pressure. The residue was extracted with methylene chloride, the organic solution was washed with water, dried over anhydrous sodium sulfate and evaporated to dryness under reduced pressure. The crude residue was purified by flash-chromatography ($SiO_2$) using methylene chloride/methanol 90/10 as eluant to give 0.11 g of the title compound (I-ag) as a white solid.

$^1$H-NMR (300 MHz, $CDCl_3$, ppm from TMS): 0.72 (3H, s); 0.94 (3H, s); 2.6–2.81 (3H, m); 2.91 (2H, t); 3.43–3.52 (2H, t); 3.64 (1H, m); 7.20–7.40 (3H, m); 7.60 (2H, d).

EXAMPLE 8

17β-Phenyl-17α-(2-(1-pyrrolidinyl)ethoxy)-5β-androstane-3β,14β-diol (I-ah)

To a solution of 0.45 g of 3β-(dimethyl-tert-butylsilyloxy)- 17β-phenyl-17α-(2-(1-pyrrolidinyl)ethoxy)-5β-androstan-14β-ol (Prepn. 2) in 5 ml of tetrahydrofuran, 1.16 g of tetrabutylammonium fluoride trihydrate were added. The resulting mixture was kept at reflux for 20 hrs, then 30 ml of water were added and the tetrahydrofuran was distilled at reduced pressure. The residue was extracted with methylene chloride, the organic layer was dried over anhydrous sodium sulfate and evaporated to dryness. The crude product was purified by flash-chromatography (SiO$_2$) using methylene chloride/methanol 85/15 as eluant to give 0.28 g of the title compound (I-ah) as a light yellow solid.

$^1$H NMR: (300 MHz, CDCl$_3$, ppm from TMS): 0.85 (3H, s); 0.93 (3H, s); 2.48–2.55 (7H, m); 3.20–3.33 (2H, m); 4.14 (1H, m); 7.20–7.40 (3H, m); 7.60 (2H, d).

EXAMPLE 9

3β,17α-Bis(2-(1-pyrrolidinyl)ethoxy)-17β-phenyl-5β-androstan-14β-ol (I-ai)

The title compound (I-ai) (0.12 g) was obtained as a white solid from 17β-phenyl-5β-androstane-3β,14β,17α-triol (I-ac) (0.10 g) using the same procedure described in Ex. 2, but keeping the reaction at reflux temperature for 24 hrs, instead of 2 hrs.

$^1$H NMR: (300 MHz, CDCl$_3$, ppm from TMS): 0.85 (3H, s); 0.93 (3H, s); 2.48–2.75 (13H, m); 3.20–3.32 (2H, m): 3.47–3.59 (2H, m); 3.63 (1H, m); 7.20–7.40 (3H, m); 7.60 (2H, d).

EXAMPLE 10

3β,17α-Bis(3-hydroxypropoxy)-17β-phenyl-5β-androstan-14β-ol (I-aj)

To a solution of 0.60 g of 17β-phenyl-5β-androstane-3β,14β,17α-triol (I-ac) in 50 ml of dry tetrahydrofuran, 1.26 g of sodium hydride (60% dispersion in mineral oil) were added under nitrogen, at room temperature and the resulting mixture was stirred at reflux temperature for 6 hrs; 4.0 g of allyl bromide were added and the reflux continued for further 8 hrs. The mixture was quenched with water and the organic solvent was distilled under reduced pressure. The residue was extracted with ethyl acetate, the organic solution was dried over anhydrous sodium sulfate and evaporated to dryness under reduced pressure. The residue was purified by flash-chromatography (SiO$_2$) using n-hexane/ethyl acetate 80/20 as eluant to give 0.58 g of 3β,17α-bis(prop-2-enoxy)-17β-phenyl-5β-androstan-14β-ol as a dense oil.

$^1$H-NMR (300 MHz, CDCl$_3$, ppm from TMS):0.87 (3H, s); 0.95 (3H, s); 3.67 (1H, m); 3.89–4.02 (4H, m); 5.08–5.25 (2H, m); 5.27–5.36 (2H, m); 5.86–6.04 (2H, m); 7.20–7.40 (3H, m); 7.60 (2H, d).

To a solution of 0.38 g of 9-borabicyclo[3.3.1]nonane in 70 ml of dry tetrahydrofuran, 0.5 g of 3β,17α-bis(prop-2-enoxy)-17β-phenyl-5β-androstan-14β-ol in 20 ml of tetrahydrofuran were added under nitrogen, at room temperature. The solution was stirred for 6 hrs, then 1.5 ml of ethanol, 0.5 ml of sodium hydroxide 6N and 1 ml of hydrogen peroxide 30% were added. The mixture was stirred at 50° C. for one hr, a solution of 1.5 g of potassium carbonate in 40 ml of water was added and the organic solvent distilled under reduced pressure. The residue was extracted with methylene chloride, the organic solution was dried over anhydrous sodium sulfate and evaporated to dryness under reduced pressure. The residue was purified by flash-chromatography (SiO$_2$) using n-hexane/ethyl acetate 70/30 as eluant to give 0.40 g of the title compound (I-aj) as a white amorphous solid.

$^1$H-NMR (300 MHz, CDCl$_3$, ppm from TMS): 0.88 (3H, s); 0.95 (3H, s); 3.57–3.68 (5H, m); 3.93–3.99 (4H, m); 7.20–7.40 (3H, m); 7.60 (2H, d).

EXAMPLE 11

3β,17α-Bis(3-aminopropoxy)-17β-phenyl-5β-androstan-14β-ol (I-ak)

A solution of 0.16 ml of diethyl azodicarboxylate was added dropwise, under nitrogen, to a solution of 0.25 g of 3β,17α-bis(3-hydroxypropoxy)-17β-phenyl- 5β-androstan-14β-ol, 0.44 g of phthalimide and 0.15 g of triphenylphosphine in 2 ml of tetrahydrofuran at room temperature. After 2 hrs the solvent was removed under reduced pressure and the crude product was purified by flash-chromatography (SiO$_2$) using n-hexane/ethyl acetate 80/20 to give 0.15 g of 3β,17α-bis(3-phthalimidopropoxy)-17β-phenyl-5β-androstan-14β-ol as a white solid.

$^1$H NMR (300 MHz, CDCl$_3$, ppm from TMS): 0.88 (3H, s); 0.95 (3H, s); 3.38–3.50 (4H, m); 3.55 (1H, m); 3.83 (4H, m); 7.20–7.40 (3H, m); 7.60 (2H, d); 7.71–7.77 (4H, m); 7.83–7.94 (4H, m).

To a solution of 0.15 g of 3β,17α-bis(3-phthalimidopropoxy)- 17β-phenyl-5β-androstan- 14β-ol in 18 ml of 96% ethanol, 0.65 g of hydrazine hydrate were added at room temperature. The mixture was kept at reflux for 4 hrs, then 10 ml of water were added and the ethanol distilled under reduced pressure. The residue was extracted with methylene chloride, the organic solution was washed with water, dried over anhydrous sodium sulfate and evaporated to dryness under reduced pressure. The crude residue was purified by flash-chromatography (SiO$_2$) using methylene chloride/methanol 90/10 as eluant to give 0.06 g of the title compound (I-ak) as a white solid.

$^1$H NMR: (300 MHz, CDCl$_3$, ppm from TMS): 0.87 (3H, s); 0.92 (3H, s); 2.82–2.96 (4H, m); 3.16–3.30 (2H, m); 3.44–3.57 (2H, m); 3.63 (1H, m); 7.20–7.40 (3H, m); 7.60 (2H, d).

EXAMPLE 12

3β-(2-(2-(1-Pyrrolidinyl)ethoxy)ethoxy)-17β-phenyl-5β-androstane-14β,17α-diol (I-al)

To a solution of 0.85 g of 3β-(2-hydroxyethoxy)-17β-phenyl-5β-androstane-14β,17α-diol (I-ad), in 9 ml of dry pyridine, 0.80 g of tosyl chloride were slowly added at room temperature. After 5 hrs 15 ml of water and 60 ml of ethyl acetate were added, the organic layer was washed with water, dried over anhydrous sodium sulfate and evaporated to dryness to give 1.08 g of 3β-(2-tosyloxyethoxy)-17β-phenyl-5β-androstane- 14β,17α-diol as a white solid.

$^1$H-NMR (300 MHz, CDCl$_3$, ppm from TMS): 0.70 (3H, s); 0.95 (3H, s); 2.10–2.30 (1H, m); 2.30–2.45 (1H, m); 2.50 (3H, s); 2.70 (1H, m); 3.52–3.62 (3H, m); 4.15–4.20 (2H, m); 7.20–7.40 (7H, m); 7.60 (2H, d).

To a suspension of 0.10 g of NaH (60% dispersion in mineral oil) in 10 ml of anhydrous dimethylformamide, 0.20 g of 1-(2-hydroxyethyl)pyrrolidine were added at room temperature in a nitrogen. The mixture was heated at 80° C. for 2 hrs, then 0.55 g of 3β-(2-tosyloxyethoxy)-17β-phenyl-5β-androstane-14β,17α-diol were added. The mixture was stirred at reflux temperature for 4 hrs; then 30 ml of water were added cautiously. The residue was extracted with methylene chloride, the organic layer was washed with water, dried over anhydrous sodium sulfate and evaporated to dryness under reduced pressure. The crude product was purified by flash-chromatography (SiO$_2$) using methylene chloride/methanol 95/5 as eluant to give 0.36 g of the title compound (I-al) as a light yellow solid.

¹H-NMR (300 MHz, CDCl₃, ppm from TMS): 0.75 (3H, s); 0.95 (3H, s); 2.10–2.30 (1H, m); 2.30–2.45 (1H, m); 2.50–2.80 (7H, m); 3.50–3.60 (2H, m); 3.60–3.70 (5H, m); 7.20–7.40 (3H, m); 7.60 (2H, d).

EXAMPLE 13

3β-(2-Methylaminoethoxy)-17β-phenyl-5β-androstane-14β,17α-diol (I-am)

To 20 ml of a solution of 3.2M methylmine in methanol, 0.25 g of 3β-(2-tosyloxyethoxy)-17β-phenyl-5β-androstane-14β,17α-diol, prepared as an intermediate in Ex. 12, were added. The solution was heated at 60° C. under nitrogen for 14 hrs and then evaporated to dryness under reduced pressure. The crude product was purified by flash-chromatography (SiO₂) using chloroform/methanol/aqueous ammonia 78/20/2 as eluant to give 0.12 g of the title compound (I-am) as a white solid.

¹H-NMR (300 MHz, CDCl₃, ppm from TMS): 0.75 (3H, s); 0.95 (3H, s); 2.10–2.30 (1H, m); 2.30–2.45 (1H, m); 2.54 (3H, s); 2.65–2.85 (3H, m); 3.00–3.10 (2H, m); 3.70 (1H, bs); 7.20–7.40 (3H, m); 7.60 (2H, d).

EXAMPLE 14

3β-(3-Guanidinopropoxy)-17β-phenyl-5β-androstane-14β,17α-diol (I-an)

To a solution of 0.23 g of 3β-(3-aminopropoxy)-17β-phenyl-5β-androstane-14β,17α-diol (I-ag) in 10 ml of absolute ethanol, 0.25 g of 3,5-dimethyl-l-pyrazolylformamidinium nitrate were added and the mixture was kept at reflux temperature for 24 hrs. The solution was evaporated to dryness and the crude product was purified by flash-chromatography (SiO₂) using chloroform/methanol/aqueous ammonia 78/20/2 as eluant to give 0.09 g of the title compound (I-an) as a white solid.

¹H NMR: (300 MHz, CDCl₃, ppm from TMS): 0.75 (3H, s); 0.95 (3H, s); 2.10–2.30 (1H, m); 2.30–2.45 (1H, m); 2.65–2.80 (1H, m); 3.15–3.30 (2H, m); 3.35–3.50 (2H, m); 7.20–7.40 (3H, m); 7.60 (2H, d).

EXAMPLE 15

3β-((2RS)-2,3-Dihydroxypropoxy)-17β-phenyl-5β-androstane-14β,17α-diol (I-ao)

To a mixture of 0.85 g of N-methylmorpholine-N-oxide, 6 ml of water, 13 ml of acetone and 2 ml of a 0.06M ethereal osmium tetroxide solution, 2.00 g of 3β-(prop-2-enoxy)-17β-phenyl-5β-androstane-14β,17α-diol, prepared as an intermediate in Ex. 6, dissolved in 25 ml of tert-butanol were added at room temperature. After 20 hrs, 50 ml of a saturated sodium hydrosulfite solution and 3 g of celite were added and the mixture was stirred for 2 hrs and then filtered. The organic solvent was distilled under reduced pressure, the aqueous phase was extracted with methylene chloride; the organic layer was dried over anhydrous sodium sulfate and evaporated to dryness under reduced pressure. The crude product was purified by flash-chromatography (SiO₂) using chloroform/methanol 95/5 as eluant to give 1.45 g of the title compound (I-ao) as a white solid.

¹H NMR (300 MHz, CDCl₃, ppm from TMS): 0.75 (3H, s); 0.95 (3H, s); 2.10–2.30 (1H, m); 2.30–2.45 (1H, m); 2.65–2.80 (1H, m); 3.45–3.60 (2H, m); 3.70 (1H, bs); 3.70–3.80 (2H, m); 3.80–3.90 (1H, m); 7.20–7.40 (3H, m); 7.60 (2H, d).

EXAMPLE 16

3β-((2RS)-2,3-Diaminopropoxy)-17β-phenyl-5β-androstane-14β,17α-diol (I-ap)

To a solution of 1.25 g of 3β-(2,3-dihydroxypropoxy)-17β-(3-furyl)-5β-androstane- 14β,17α-diol (I-ao), in 6.00 ml of dry pyridine, 0.80 g of tosyl chloride were added at a temperature of 0° C. After 6 hrs 15 ml of water and 50 ml of ethyl acetate were added; the organic layer was separated and washed with water, dried over anhydrous sodium sulfate and evaporated to dryness. The crude product was purified by flash-chromatography (SiO₂) using n-hexane/ethyl acetate 70/30 as eluant to give 1.25 g of 3β-(2,3-ditosyloxypropoxy)-17β-phenyl-5β-androstane-14β,17α-diol as a white solid.

¹H NMR (300 MHz, CDCl₃, ppm from TMS): 0.75 (3H, s); 0.95 (3H, s); 2.10–2.30 (1H, m); 2.30–2.40 (1H, m); 2.45 (6H, bs); 2.65–2.80 (1H, m); 3.45–3.55 (3H, m); 4.05–4.15 (2H, m); 4.60 (1H, bs); 7.20–7.40 (3H, m); 7.60 (2H, d).

To a solution of 1.20 g of 3β-(2,3-ditosyloxypropoxy)-17β-phenyl-5β-androstane- 14β,17α-diol in 10 ml of dimethylsulfoxide, 1.00 g of sodium azide was added at room temperature. The solution was heated at reflux temperature for 3 hrs. After cooling 35 ml of water were added and the residue was extracted with methylene chloride. The organic layer was washed with water, dried over anhydrous sodium sulfate and evaporated to dryness. The crude product was purified by flash-chromatography (SiO₂) using n-hexane/ethyl acetate 70/30 as eluant to give 0.61 g 3β-(2,3-diazidopropoxy)-17β-phenyl-5β-androstane- 14β,17α-diol.

¹H NMR: (300 MHz, CDCl₃, ppm from TMS): 0.75 (3H, s); 0.95 (3H, s); 2.10–2.30 (1H, m); 2.30–2.40 (1H, m); 2.65–2.80 (1H, m); 3.40–3.70 (6H, m); 7.20–7.40 (3H, m); 7.60 (2H, d).

A solution of 0.55 g of 3β-(2,3-diazidopropoxy)-17β-phenyl-5β-androstane-14β,17α-diol in 10 ml of diethyl ether is added to a suspension of 0.15 g of lithium aluminum hydride in 5 ml of diethyl ether. The mixture was heated at reflux temperature for 10 hrs then in succession were added 0.30 ml of water, 0.30 ml of sodium hydroxyde ( water solution 10%) and 1.5 ml of water. The mixture was filtered over a celite cake, the organic solution was washed with water, dried over anhydrous sodium sulfate and evaporated to dryness. The crude residue was purified by flash-chromatography (SiO₂) using methylene chloride/methanol/30% ammonia solution 78/20/2 as eluant to give 0.24 g of the title compound (I-ap) a white solid.

¹H NMR (300 MHz, CDCl₃, ppm from TMS): 0.75 (3H, s); 0.95 (3H, s); 2.10–2.30 (1H, m); 2.30–2.40 (1H, m); 2.65–3.50 (6H, m); 3.70 (1H, bs); 7.20–7.40 (3H, m); 7.60 (2H, d).

EXAMPLE 17

14β,17α-Dihydroxy-17β-phenyl-5β-androstan-3-one (I-aq)

To a solution of 3.0 g of 17β-phenyl-5β-androstane-3β, 14β,17α-triol (I-ac) in 50 ml of methylene chloride, 1.40 g of 4-methylmorpholine N-oxide, 0.15 g of tetrapropylammonium perruthenate and 3.0 g of powdered 4 Å molecular sieves were added at room temperature. After 4 hrs the solvent was evaporated to dryness under reduced pressure and the crude product purified by flash-chromatography (SiO₂) using n-hexane/ethyl acetate 70/30 as eluant to give 2.90 g of the title compound (I-aq) as a white solid.

¹H-NMR (300 MHz, CDCl₃, ppm from TMS): 0.73 (3H, s); 0.98 (3H, s); 2.70 (1H, t); 7.20–7.40 (3H, m); 7.61 (2H, d).

EXAMPLE 18

3-Guanidinoimino-17β-phenyl-5β-androstane-14β,17α-diol (I-ar)

A solution of 0.35 g of 14β,17α-dihydroxy-17β-phenyl-5β-androstan-3-one (I-aq) in 5 ml of ethanol was added to a solution of 0.26 g of aminoguanidine bicarbonate and 19 ml of NaOH 0.1N. The resulting mixture was kept at reflux for half one hr, then the ethanol was evaporated. The precipitate was filtered, washed with water, then with diethyl ether and dried by heating at 60° C. under reduced pressure to give 0.36 g of the title compound (I-at) as a white solid.

¹H-NMR (300 MHz, DMSO-d₆, ppm from TMS): 0.56 (3H, s); 0.82 (3H, s); 3.57 (1H, s); 4.56 (1H, s); 5.04 (2H, bb): 5.46 (2H,bb); 7.10–7.20 (3H, m); 7.41 (2H, d).

EXAMPLE 19

17β-(4-Methoxyphenyl)-5β-androst-15-ene-3β,14β,17α-triol (I-as)

To a solution of 6.20 ml of 4-bromoanisole in 50 ml of dry ether, at −30° C., under nitrogen, 31 ml of n-butyllithium (solution 1.6M in hexane) were added. After 24 hrs the resulting mixture was added to a suspension of 12.3 g of anhydrous CeCl₃ in 40 ml of dry tetrahydrofuran and the suspension was kept at the same temperature for 6 hrs, then 5.03 g of 3β,14β-dihydroxy-5β-androst-15-en-17-one (G. Groszek et al., *Bull. Pol. Acad. Sci., Chem.*, 34, 1986, 313) were added to the mixture. After 8 hrs the reaction mixture was diluted with 150 ml of water, filtered through celite and extracted with ethyl acetate; the combined organic layer were dried over anhydrous sodium sulfate and evaporated to dryness under reduced pressure. The crude product was purified by flash-chromatography (SiO₂) using ethyl acetate/cyclohexane 70/30 as eluant to give 2.10 g of the title compound (I-as) as a white solid.

¹H-NMR (300 MHz, CDCl₃, ppm from TMS): 0.85 (3H, s); 0.95 (3H, s); 3.80 (3H, s); 4.15 (1H, m); 5.95 (1H, d); 6.45 (1H, d); 6.85 (2H, d); 7.38 (2H, d).

EXAMPLE 20

3β-(2-(1-Pyrrolidinyl)ethoxy)-17β-(4-methoxyphenyl)-5β-androst-15-ene- 14β,17α-diol (I-at)

The title compound (I-at) (0.25 g) was obtained as a white solid from 17β-(4-methoxyphenyl)-5β-androst-15-ene-3β, 14β,17α-triol (I-as) (0.60 g) and 1-(2-chloroethyl)pyrrolidine using the same procedure described in Ex. 2.

¹H-NMR (300 MHz, CDCl₃, ppm from TMS): 0.85 (3H, s); 0.95 (3H, s); 2.53–2.71 (6H, m); 3.48–3.59 (2H, m); 3.63 (1H, m); 3.80 (3H, s); 5.95 (1H, d); 6.45 (1H, d); 6.85 (2H, d); 7.38 (2H, d).

EXAMPLE 21

17β-(4-Methoxyphenyl)-5β-androstane-3β,14β,17α-triol (I-au)

The title compound (I-au) (0.30 g) was obtained as a white solid from 17β-(4-methoxyphenyl)-5β-androst-15-ene-3β,14β,17α-triol (I-as) (0.32 g) using the same procedure described in Ex. 3.

¹H-NMR (300 MHz, CDCl₃, ppm from TMS): 0.70 (3H, s); 0.98 (3H, s); 2.19 (1H, m); 2.35 (1H, m); 2.70 (1H, m): 3.80 (3H, s); 4.16 (1H, m); 6.85 (2H, d); 7.50 (2H, d).

EXAMPLE 22

3β-(2-Diethylaminoethory)-17β-(4-methoxyphenyl)-5β-androstane-14β,17α-diol (I-av)

The title compound (I-av) (0.21 g) was obtained as a white solid from 17β-(4-methoxyphenyl)-5β-androstane-3β, 14β,17α-triol (I-au) (0.90 g) and 2-chloro-N,N-diethylaminoethane using the same procedure described in Ex. 2.

¹H-NMR (300 MHz, CDCl₃, ppm from TMS): 0.70 (3H, s); 0.98 (3H, s); 2.19 (1H, m); 2.35 (1H, m); 2.53–2.72 (7H, m); 3.48–3.60 (2H, m); 3.63 (1H, m); 3.80 (3H, s); 6.85 (2H, d ); 7.50 (2H, d).

EXAMPLE 23

14β,17α-Dihydroxy-17β-(4-methoxyphenyl)-5β-androstan-3-one (I-aw)

The title compound (I-aw) (0.25 g) was obtained as a white solid from 17β-(4-methoxyphenyl)-5β-androstane-3β, 14β,17α-triol (I-au) (0.27 g) using the same procedure described in Ex. 17.

¹H-NMR (300 MHz, CDCl₃, ppm from TMS): 0.70 (3H, s); 1.00 (3H, s); 2.19 (1H, m); 2.35 (1H, m); 2.68–2.72 (2H, m); 3.80 (3H, s); 6.85 (2H, d ); 7.50 (2H, d).

EXAMPLE 24

3-Guanidinoimino-17β-(4-methoxyphenyl)-5β-androstane-14β,17α-diol (I-ax)

The title compound (I-ax) (0.25 g) was obtained as a white solid from 14β,17α-dihydroxy-17β-(4-methoxyphenyl)-5β-androstan-3-one (I-aw) (0.25 g) using the same procedure described in Ex. 18.

¹H-NMR (300 MHz, DMSO-d₆, ppm from TMS): 0.56 (3H, s); 0.84 (3H, s); 3.57 (1H, s); 3.75 (3H, s); 4.56 (1H, s); 5.04 (2H, bb); 5.46 (2H,bb); 6.21 (2H, d); 7.40 (2H, d).

EXAMPLE 25

17β-(4-Hydroxyphenyl)-5β-androstane-3β,14β,17α-triol (I-ay)

The title compound (I-ay) (0.95 g) was obtained as a white solid from 1.30 g of 17β-(4-benzyloxyphenyl)-5β-androst-15-ene-3β,14β,17α-triol, using the same procedure described in Ex. 3, which in turn was obtained from 3β,14β-dihydroxy-5β-androst-15-en-17-one (G. Groszek et al., *Bull. Pol. Acad. Sci., Chem.*, 34, 1986, 313) (1.60 g) and 4-benzyloxybromobenzene as described in Ex. 19.

¹H-NMR (300 MHz, CDCl₃, ppm from TMS): 0.71 (3H, s); 0.99 (3H, s); 2.19 (1H, m); 2.35 (1H, m); 2.70 (1H, m); 4.16 (1H, m); 6.82 (2H, d ) 7.53 (2H, d).

EXAMPLE 26

17β-(4-Chlorophenyl)-5β-androstane-3β,14β,17α-triol (I-az)

The title compound (I-az) (1.0 g) was obtained as a white solid from 1.10 g of 17β-(4-chlorophenyl)-5β-androst-15-ene-3β,14β,17α-triol using the same procedure described in Ex. 3, but keeping the temperature at 0° C. to selectively reduce the double bond. The starting 15-ene compound was in turn obtained from 3β,14β-dihydroxy-5β-androst-15-en-17-one (G. Groszek et al., *Bull. Pol. Acad. Sci. Chem.*, 34, 1986, 313) (1.50 g) and the organometallic derivative obtained from 4-bromochlorobenzene as described in Ex. 19.

$^1$H-NMR (300 MHz, CDCl$_3$, ppm from TMS): 0.75 (3H, s); 0.98 (3H, s); 2.18(1H, m); 2.39 (1H, m); 2.70 (1H, m); 4.16 (1H, m); 7.15–7.48 (4H, m).

EXAMPLE 27

17β-(3-Thienyl)-5β-androstane-3β,14β,17α-triol (I-ba)

The title compound (I-ba) (1.5 g) was obtained as a white solid from 17β-(3-thienyl)-5β-androst-15-ene-3β,14β,17α-triol (2.0 g), using the same procedure described in Ex. 3, but the reaction was shaken with H$_2$ for a week and the PtO$_2$ was added every day. 17β-(3-thienyl)- 5β-androst-15-ene-3β,14β,17α-triol was obtained from 3β,14β-dihydroxy-5β-androst-15-en-17-one (G. Groszek et al., *Bull. Pol. Acad. Sci., Chem.*, 34, 1986, 313) (2.50 g) and 3-bromothiophene as described in Ex. 19.

$^1$H-NMR (300 MHz, CDCl$_3$, ppm from TMS): 0.80 (3H, s); 0.98 (3H, s); 2.69 (1H, m); 4.15 (1H, m); 7.12 (1H, m); 7.21 (1H, m); 7. 35 (1H, m).

EXAMPLE 28

17β-(3-Pyridyl)-5β-androstane-3β,14β,17α-triol (I-bb)

The title compound (I-bb) (0.76 g) was obtained as a white solid from 17β-(3-pyridyl)-5β-androst-15-ene-3β,14β,17α-triol (0.90 g), using the same procedure described in Ex. 3, which in turn was obtained from 3β,14β-dihydroxy-5β-androst-15-en-17-one (G. Groszek et al., *Bull. Pol. Acad. Sci., Chem.*, 34, 1986, 313) (1.20 g) and 3-bromopyridine as described in Ex. 19.

$^1$H-NMR (300 MHz, CDCl$_3$, ppm from TMS): 0.80 (3H, s); 0.98 (3H, s): 2.68 (1H, m):4.15 (1H, m); 7.21 (1H, m); 7.81 (1H, m); 8.48 (1H, m): 8.68 (1H, m).

EXAMPLE 29

17β-(3-Pyridyl-N-oxide)-5β-androstane-3β,14β,17α-triol (I-bc)

A solution of 0.35 g of 17β-(3-pyridyl)-5β-androstane-3β,14β,17α-triol (I-bb) in 15 ml of chloroform was treated with 0.30 g of m-chloroperbenzoic acid at room temperature for 24 hrs. The mixture was then treated with aqueous sodium hydrogen carbonate and extracted with chloroform. The organic phase was dried over anhydrous sodium sulfate and evaporated to dryness under reduced pressure. The crude product was purified by flash-chromatography (SiO$_2$) using chloroform/methanol/aqueous ammonia 78/20/2 as eluant to give 0.15 g of the title compound (I-bc), as a white solid.

$^1$H-NMR (300 MHz, CDCl$_3$, ppm from TMS): 0.80 (3H, s); 0.98 (3H, s); 2.68 (1H, m);4.15 (1H, m): 7.50 (1H, m): 8.10 (1H, m); 8.75 (1H, m); 9.00 (1H, m).

EXAMPLE 30

17β-(2-Thiazolyl)-5β-androstane-3β,14β,17α-triol (I-bd)

To a solution of 3.70 g of thiazole in 300 ml of dry diethyl ether, cooled at −60° C., 22 ml of 1.6M n-butyllithium in hexane were added. After 2 hrs a solution of 1.00 g of 3β-hydroxy-14β-ethoxymethoxy-5β-androst-15-en- 17-one (Prepn. 1) in 100 ml of dry diethyl ether was added and the mixture was stirred at −60° C. for 8 hrs. The reaction was allowed to come to room temperature overnight and then was poured into water. The organic layer was dried over anhydrous sodium sulfate and evaporated to dryness under reduced pressure. The crude product was purified by flash-chromatography (SiO$_2$) using ethyl acetate as eluant to give 0.55 g of 17β-(2-thiazolyl)-14β-ethoxymethoxy- 5β-androst-15-ene-3β,17α-diol as a white solid.

$^1$H-NMR (300 MHz, CDCl$_3$, ppm from TMS): 0.80 (3H, s); 0.95 (3H, s); 3.45 (1H, m); 4.15 (1H, m); 4.40 (1H, d); 4.50 (1H, dd); 6.10 (1H, d); 6.45 (1H, d); 7.70 (1H, m); 8.70 (1H, m).

0.55 g of 17β-(2-thiazolyl)-14β-ethoxymethoxy-5β-androst-15-ene-3β,17α-triol were hydrogenated as described in Ex. 3 to give 0.50 g of 17β-(2-thiazolyl)-14β-ethoxymethoxy-5β-androstane-3β,17α-diol.

$^1$H-NMR (300 MHz, CDCl$_3$, ppm from TMS): 0.70 (3H, s); 0.95 (3H, s); 2.40 (1H, m); 2.65 (1H, m); 3.25 (1H, dd): 3.60 (1H, dd); 3.95 (1H, d); 4.15 (1H, m): 4.60 (1H, d): 7.70 (1H, m); 8.70 (1H, m).

A solution of 0.50 g 17β-(2-thiazolyl)-14β-ethoxymethoxy-5β-androstane-3β,17α-triol in 9 ml of acetonitrile and 1 ml of water was added with p-toluensulfonic acid until pH 1.1 was reached. After 20 hrs at room temperature the mixture was diluted with water and extracted with chloroform. The organic phase was dried over anhydrous sodium sulfate and evaporated to dryness under reduced pressure. The crude product was purified by flash-chromatography (SiO$_2$) using chloroform/methanol/aqueous ammonia 89/10/1 as eluant to give 0.20 g of the title compound (I-bd) as a white solid.

$^1$H-NMR (300 MHz, CDCl$_3$, ppm from TMS): 0.70 (3H, s); 0.95 (3H, s): 2.35 (1H, m); 2.70 (1H, m); 4.15 (1H, m): 7.70 (1H, m); 8.70 (1H, m).

EXAMPLE 31

17β-(1,2-Dimethyl-5-imidazolyl)-5β-androstane-3β,14β,17α-triol (I-be).

The title compound (I-be) (0.08 g) was obtained as a white solid from 1.70 g of 3β-hydroxy-14β-ethoxymethoxy-5β-androst-15-en-17-one (Prepn. 1), using the same procedure described in Ex. 30 and 1,2-dimethylimidazole.

$^1$H-NMR (300 MHz, CDCl$_3$, ppm from TMS): 0.70 (3H, s); 0.95 (3H, s); 2.35 (1H, m); 2.40 (3H, s): 2.70 (1H, m); 3.60 (3H, s); 4.15 (1H, m); 7.00 (1H, m).

EXAMPLE 32

17β-(4-(N,N-Dimethylaminophenyl))-5β-androstane-3β,14β,17α-triol (I-bf)

The title compound (I-bf) (0.28 g) was obtained as a white solid from 1.20 g of 3β-hydroxy-14β-ethoxymethoxy-5β-androst-15-en-17-one (Prepn. 1), using the same procedure described in Ex. 30 and 4-bromo-N,N-dimethylaniline.

$^1$H-NMR (300 MHz, CDCl$_3$, ppm from TMS): 0.70 (3H, s); 0.95 (3H, s); 2.35 (1H, m): 2.70 (1H, m); 4.15 (1H, m); 6.80 (2H, m); 7.20 (2H, m).

EXAMPLE 33

17β-(2-Furyl)-5β-androstane-3β,14β,17α-triol (I-bg)

The title compound (I-bg) (0.22 g) was obtained as a white solid from 1.50 g of 3β-hydroxy-14β-ethoxymethoxy-5β-androst-15-en-17-one (Prepn. 1), using the same procedure described in Ex. 30 and furan and carrying out the hydrogenation over Raney Nickel.

$^1$H-NMR (300 MHz, CDCl$_3$, ppm from TMS): 0.70 (3H, s); 0.95 (3H, s); 2.35 (1H, m); 2.70 (1H, m); 4.15 (1H, m): 6.30 (2H, m): 7.30 (1H, m).

EXAMPLE 34

17β-Phenyl-5β-androstane-3α,14β,17α-triol (I-bh)

To a solution of 6.00 g of 14β,17α-dihydroxy-17β-phenyl-5β-androstan-3-one (I-aq) in 40 ml of dry tetrahydrofuran at −78° C., a solution of 13.10 g of tri-tert-butoxyaluminum hydride in dry tetrahydrofuran was added dropwise. The mixture was stirred for 20 hrs, the temperature raised to 25° C., then 80 ml of water were added. The aluminum salts were filtered on a celite cake and washed with methanol. The solution was filtered, concentrated under reduced pressure and extracted with methylene chloride. The organic layer was dried over anhydrous sodium sulfate and evaporated to dryness under reduced pressure to give 5.60 g of the title compound (I-bh) as a white solid.

$^1$H-NMR (300 MHz, CDCl$_3$, ppm from TMS): 0.70 (3H, s); 0.95 (3H, s); 3.60–3.75 (1H, m); 7.20–7.40 (3H, m); 7.60 (1H, d).

EXAMPLE

3β-Mercapto-17β-phenyl-5β-androstan-14β,17α-diol (I-bi)

Diisopropyl azodicarboxylate (8.9 ml) was added to a solution of 11.2 g of triphenylphosphine in 200 ml of tetrahydrofuran at 0° C. and the mixture was stirred for 30'. To this mixture a solution of 5.10 g of 17β-phenyl-5β-androstane-3α,14β,17α-triol (I-bh) and 5.20 ml of thiolacetic acid in 250 ml of tetrahydrofuran was added dropwise and the resulting mixture was stirred for one hr at room temperature. The solvent was evaporated to dryness under reduced pressure and the crude product was purified by flash-chromatography (SiO$_2$) using n-hexane/ethyl acetate 85/15 as eluant to give 4.05 g of 3β-acetylthio-17β-phenyl-5β-androstan-14β,17α-diol as a white solid.

$^1$H-NMR (300 MHz, CDCl$_3$, ppm from TMS): 0.70 (3H, s); 0.95 (3H, s); 2.25–2.35 (4H, m); 2.60 (1H, d); 2.70 (1H, m); 4.10 (1H, bs); 7.20–7.40 (3H, m); 7.60 (1H, d).

A solution of 4.00 g of 3β-acetylthio-17β-phenyl-5β-androstan-14β,17α-diol in 50 ml of methanol, was saturated with gaseous ammonia and kept for 3 hrs at room temperature. The mixture was evaporated to dryness under reduced pressure and purified by flash-chromatography (SiO$_2$) using n-hexane/ethyl acetate 75/25 as eluant to give 3.15 g of the title compound (I-bi) as a white solid.

$^1$H-NMR (300 MHz, CDCl$_3$, ppm from TMS): 0.70 (3H, s); 0.95 (3H, s); 2.20 (1H, d); 2.60 (1H, d); 3.60 (1H, m); 7.20–7.40 (3H, m); 7.60 (1H, d).

EXAMPLE 36

3β-(3-Aminopropylthio)-17β-phenyl)-5β-androstan-14β,17α-ol (I-bj)

To a solution of 1.20 g of 3β-mercapto-17β-phenyl-5β-androstan-14β,17α-diol (I-bi) and 0.70 ml of 3-chloropropylamine in 10 ml of tetrahydrofuran under nitrogen, at room temperature, 0.063 g of sodium hydride (60% dispersion in mineral oil) were added. The reaction mixture was stirred for 40 hrs at room temperature then diluted with water and extracted with ethyl acetate. The organic layer was dried over anhydrous sodium sulfate and evaporated to dryness under reduced pressure. The crude product was purified by flash-chromatography (SiO$_2$) using methylene chloride/methanol/30% ammonia solution 95/5/1 as eluant and successively treated with oxalic acid to give 0.40 g of the title compound (I-bj) as a white solid.

$^1$H-NMR (300 MHz, CDCl$_3$, ppm from TMS): 0.75 (3H, s); 1.00 (3H, s); 2.33 (1H, m); 2.50–2.65 (3H, m); 2.70 (1H, m); 2.80 (2H, t); 3.25 (1H, m); 7.20–7.40 (3H, m); 7.60 (1H, d).

EXAMPLE 37

3β-(2-(1-Pyrrolidinyl)ethylthio)-17β-(phenyl)-5β-androstan-14β,17α-ol (I-bk)

The title compound (I-bk) (0.25 g) was obtained as a pale yellow solid from 0.45 g of 3β-mercapto-17β-phenyl-5β-androstan-14β,17α-diol (I-bi) and 1-(2-chloroethyl)pyrrolidine (0.75 g) using the same procedure described in Ex. 36.

$^1$H-NMR (300 MHz, CDCl$_3$, ppm from TMS): 0.70 (3H, s); 0.95 (3H, s); 2.50–2.60 (5H, m): 2.65–2.75 (5H, m); 3.25 (1H, bs); 3.76 (1H, bs); 7.20–7.40 (3H, m): 7.60 (1H, d).

PREPARATION OF INTERMEDIATES

Preparation 1

3β-Hydroxy-14β-ethoxymethoxy-5β-androst-15-en-17-one (II-a)

A solution of 9.20 g of 3β-acetoxy-14β-hydroxy-5β-androst-15-en-17-one (G. Groszek et al., *Bull. Pol. Acad. Sci., Chem.*, 34, 1986, 313), 11 ml of ethyl chloromethyl ether, 54 ml of diisopropylethylamine in 750 ml of dichloromethane was heated at reflux for 24 hrs. The solution was then cooled and poured into 500 ml of aq. 8% citric acid solution. The lower layer was separated, washed with water, dried over anhydrous sodium sulfate and evaporated to dryness. The crude product was purified by chromatography using cyclohexane/chloroform/acetone 80/10/10 as eluant to give 6.10 g of 3β-acetoxy-14β-ethoxymethoxy-5β-androst-15-en-17-one, as a white solid.

¹H-NMR (300 MHz, CDCl₃, ppm from TMS); 0.90 (3H, s); 1.00 (3H, s); 2.00 (3H, s); 3.50 (1H, m); 3.80 (1H, m); 4.40 (1H, d); 4.55 (1H, d}; 5.10 (1H, m); 6.40 (1H, d); 7.70 (1H, d).

A solution of 6.00 g of 3β-acetoxy-14β-ethoxymethoxy-5β-androst-15-en-17-one and 30 ml of 2N aq. sodium hydroxide in 120 ml of methanol was kept at room temperature for 24 hrs. The mixture was then diluted with water and extracted with dichloromethane. The organic phase was dried over anhydrous sodium sulfate and evaporated to dryness to give 4.90 g of the title compound (II-ac) as a white solid.

¹H-NMR (300 MHz, CDCl₃, ppm from TMS): 0.90 (3H, s); 1.00 (3H, s); 3.50 (1H, m); 3.80 (1H, m); 4.10 (1H, m); 4.40 (1H, d); 4.55 (1H, d); 6.40 (1H, d); 7.70 (1H, d).

Preparation 2

3β-(Dimethyl-tert-butylsilyloxy)-17β-phenyl-17α-(2-(1-pyrrolidinyl)ethoxy)-5β-androstan-14β-ol (II-b)

To a solution of 1.0 g of dimethyl-tert-butylsilylchloride and 0.91 g of imidazole in 3 ml of dry dimethylformamide, 0.51 g of 17β-phenyl-5β-androstane-3β,14β,17α-triol (I-c) were added under nitrogen, at room temperature. The resulting mixture was stirred for 6 hrs, then it was diluted with water and extracted with ethyl acetate; the combined extracts were dried over anhydrous sodium sulfate and evaporated to dryness under reduced pressure. The crude product was purified by flash-chromatography (SiO₂) using cyclohexane/ethyl acetate 95/5 as eluant to give 0.46 g of the title compound 3β-(dimethyl-tert-butylsilyloxy)-17β-phenyl- 5β-androstane-14β,17α-diol as a white solid.

¹H-NMR (300 MHz, CDCl₃, ppm from TMS): 0.03 (6H, s); 0.71 (3H, s); 0.91 (9H, s); 0.95 (3H, s); 2.68 (1H, s); 4.04 (1H, m); 7.20–7.40 (3H, m); 7.61 (2H, d).

To a suspension of 0.35 g of NaH (60% dispersion in mineral oil) in 30 ml of dry tetrahydrofuran 0.43 g of 3β-(dimethyl-tert-butylsilyloxy)- 17β-phenyl-5β-androstane-14β,17α-diol were added at room temperature, under nitrogen. The mixture was refluxed for 6 hrs, then 1.35 g of 1-(2-chloroethyl)pyrrolidine were added; the suspension was refluxed for 4 hrs, then 25 ml of water were added cautiously and the tetrahydrofuran was distilled at reduced pressure. The residue was extracted with methylene chloride, the organic layer was dried over anhydrous sodium sulfate and evaporated to dryness under reduced pressure. The crude product was purified by flash-chromatography (SiO₂) using methylene chloride/methanol 90/10 as eluant to give 0.35 g of the title compound (II-b) as a white solid.

¹H-NMR (300 MHz, CDCl₃, ppm from TMS): 0.03 (6H, s); 0.92 (3H, s); 0.91 (9H, s); 0.99 (3H, s): 2.48–2.52 (6H, m): 3.19–3.31 (2H, m); 4.04 (1H, m); 7.20–7.40 (3H, m); 7.61 (2H, d).

We claim:

1. 17-Aryl and 17-heterocyclyl-5β,14β-androstane compounds of formula (I):

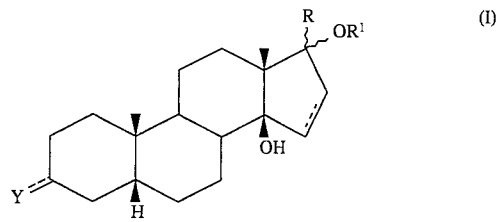

wherein:

the symbol ⌇ means that the substituents in position 17 have an α or β configuration;

the symbol --- represents a single or a double bond;

Y is oxygen or guanidinoimino, when --- in position 3 is a double bond;

Y is hydroxy, OR² or SR², when --- in position 3 is a single bond and has an α or β configuration;

R is an aryl ring, unsubstituted or substituted by one or more halogen, hydroxy, hydroxymethyl, alkoxy, oxo, amino, alkylamino, dialkylamino, cyano, nitro, sulfonamido, C1-C6 lower alkyl group or COR³;

R¹ is hydrogen; methyl; ethyl or n-propyl substituted by OH or NR⁴R⁵;

R² is hydrogen; methyl; C2-C6 alkyl or C3-C6 alkenyl or C2-C6 acyl, unsubstituted or substituted by a quaternary ammonium group or one or more OR⁶, NR⁷R⁸, CHO, C(NH)NH₂, guanidinoimino or by NR⁷R⁸ and hydroxy;

R³ is hydrogen, hydroxy, C1-C4 alkoxy or C1-C4 alkyl;

R⁴, R⁵ are independently hydrogen; methyl, C2-C6 alkyl unsubstituted or substituted by NR⁹R¹⁰, or R⁴ and R⁵ taken together with the nitrogen atom form an unsubstituted or substituted saturated or unsaturated five- or six-membered ring optionally containing another heteroatom selected from the group consisting of oxygen, sulfur and nitrogen;

R⁶ is hydrogen; methyl; C2-C4 alkyl, unsubstituted or substituted by one or more NR⁹R¹⁰ or by NR⁹R¹⁰ and hydroxy;

R⁷, R⁸ are independently hydrogen; methyl; C2-C6 alkyl or C3-C6 alkenyl unsubstituted or substituted by one or more NR⁹R¹⁰, or NR⁹R¹⁰ and hydroxy, or R⁷ and R⁸ taken together with the nitrogen atom they are linked to, form an unsubstituted or substituted saturated or unsaturated five- or six-membered ring optionally containing another heteroatom selected from the group consisting of oxygen, sulfur and nitrogen, or R⁷ is hydrogen and R⁸ is C(NH)NH₂;

R⁹, R¹⁰ are independently hydrogen, C1-C6 alkyl, or R⁹ and R¹⁰ taken together with the nitrogen atom they are linked to, form a saturated or unsaturated five- or six-membered ring.

2. Stereoisomers, Z and E isomers, tautomers, optical isomers and mixtures thereof and pharmaceutically acceptable salts of compounds of formula (I) of claim 1.

3. A compound according to claim 1, which is selected from the group consisting of:

17β-Phenyl-5β-androst-15-ene-3β,14β,17α-triol

3β-(2-(1-Pyrrolidinyl)ethoxy)-17β-phenyl-5β-androst-15-ene-14β,17α-diol

17β-Phenyl-5β-androstane-3β,14β,17α-triol

3β-(2-(1-Pyrrolidinyl)ethoxy)-17β-phenyl-5β-androstane-14β,17α-diol

17β-Phenyl-17α-(2-(1-pyrrolidinyl)ethoxy)-5β-androstane-3β,14β-diol

3β,17α-Bis(2-(1-pyrrolidinyl)ethoxy)-17β-phenyl-5β-androstane-14β-ol
17β-(2-Methoxyphenyl)-5β-androstane-3β,14β,17α-triol
3β-(2-(1-Pyrrolidinyl)ethoxy)-17β-(2-methoxyphenyl)-5β-androstane-14β,17α-diol
17β-(2-Methoxyphenyl)-17α-(2-(1-pyrrolidinyl)ethoxy)-5β-androstane-3β,14β-diol
3β,17α-Bis(2-(1-pyrrolidinyl)ethoxy)-17β-(2-methoxyphenyl)-5β-androstane-14β-ol
17β-(3-Methoxyphenyl)-5β-androstane-3β,14β,17α-triol
3β-(2-(1-Pyrrolidinyl)ethoxy)-17β-(3-methoxyphenyl)-5β-androstane-14β,17α-diol
17β-(3-Methoxyphenyl)-17α-(2-(1-pyrrolidinyl)ethoxy)-5β-androstane-3β,14β-diol
3β,17α-Bis(2-(1-pyrrolidinyl)ethoxy)-17β-(3-methoxyphenyl)-5β-androstane-14β-ol
17β-(4-Methoxyphenyl)-5β-androst-15-ene-3β,14β,17α-triol
3β-(2-(1-Pyrrolidinyl)ethoxy)-17β-(4-methoxyphenyl)-5β-androst-15-ene-14β,17α-diol
17β-(4-Methoxyphenyl)-5β-androstane-3β,14β,17α-triol
3β-(2-(1-Pyrrolidinyl)ethoxy)-17β-(4-methoxyphenyl)-5β-androstane-14β,17α-diol
17β-(4-Methoxyphenyl)-17α-(2-(1-pyrrolidinyl)ethoxy)-5β-androstane-3β,14β-diol
3β,17α-(Bis(2-(1-pyrrolidinyl)ethoxy)-17β-(4-methoxyphenyl)-5β-androstane-14β-ol
17β-(3-Hydroxyphenyl)-5β-androstane-3β,14β,17α-triol
17β-(4-Hydroxyphenyl)-5β-androstane-3β,14β,17α-triol
17β-(4-Methylphenyl)-5β-androstane-3β,14β,17α-triol
3β-(2-(1-Pyrrolidinyl)ethoxy)-17β-(4-methylphenyl)-5β-androstane-14β,17α-diol
17β-(4-Methylphenyl)-17α-(2-(1-pyrrolidinyl)ethoxy)-5β-androstane-3β,14β-diol
3β,17α-Bis(2-(1-pyrrolidinyl)ethoxy)-17β-(4-methylphenyl)-5β-androstane-14β-ol
17β-(4-Chlorophenyl)-5β-androstane-3β,14β,17α-triol
3β-(2-(1-Pyrrolidinyl)ethoxy)-17β-(4-chlorophenyl)-5β-androstane-14β,17α-diol
17β-(4-Chlorophenyl)-17α-(2-(1-pyrrolidinyl)ethoxy)-5β-androstane-3β,14β-diol
3β,17α-Bis(2-(1-pyrrolidinyl)ethoxy)-17β-(4-chlorophenyl)-5β-androstane-14β-ol
17β-(4-Cyanophenyl)-5β-androstane-3β,14β,17α-triol
17β-(2-Nitrophenyl)-5β-androstane-3β,14β,17α-triol
17β-(4-Dimethylaminophenyl)-5β-androstane-3β,14β,17α-triol and
17β-(4-Carboxyphenyl)-5β-androstane-3β,14β,17α-triol and the corresponding 3β-(2-hydroxyethoxy), 3β-(3-hydroxypropoxy), 3β-(2,3-dihydroxypropoxy), 3β-(2-aminoethoxy), 3β-(3-aminopropoxy), 3β-(2-methylaminoethoxy), 3β-(3-methylaminopropoxy), 3β-(2-dimethylaminoethoxy), 3β-(3-dimethylaminopropoxy), 3β-(2-diethylaminoethoxy), 3β-(3-diethylaminopropoxy), 3β-(3-(1-pyrrolidinyl)propoxy), 3β-(2,3-diaminopropoxy), 3β-(2-(2-(1-pyrrolidinyl)ethoxy)ethoxy), 3β-(2-guanidinoethoxy), 3β-(3-guanidinopropoxy) of the 3β-(2-(1-pyrrolidinyl)ethoxy) compounds;

and the corresponding 17β-(2-hydroxyethoxy), 17α-(3-hydroxypropoxy), 17α-(2-aminoethoxy), 17α-(3-aminopropoxy), 17α-(3-(1-pyrrolidinyl)propoxy of the 17α-(2-(1-pyrrolidinyl)ethoxy) compounds;

and the corresponding 3-oxo and 3-guanidinoimino of the corresponding 3β-ol compounds;

and the corresponding 3β,17α-bis-(2-hydroxyethoxy), 3β,17α-bis-(3-hydroxypropoxy), 3β,17α-bis-(2,3-dihydroxypropoxy), 3β,17α-bis-(2-aminoethoxy), 3β,17α-bis-(3-aminopropoxy) of the corresponding 3β,17α-bis(2-(1-pyrrolidinyl)ethoxy) compounds;

and the corresponding 3β-(2-aminoethylthio), 3β-(3-aminopropylthio), 3β-(2-(1-pyrrolidinyl)ethylthio), 3β-(3-(1-pyrrolidinyl)propylthio), 3β-(2-(2-(1-pyrrolidinyl)ethoxy)ethylthio) of the 3β-(2-(1-pyrrolidinyl)ethoxy) compounds.

4. An antihypertensive pharmaceutical composition containing a compound of formula (I) of claim 1 with a pharmaceutically acceptable carrier and/or diluent.

5. A compound according to claim 1, wherein R is unsubstituted phenyl or naphthyl.

6. A compound according to claim 1, wherein R is phenyl or naphthyl substituted with a substituent selected from the group consisting of methyl, ethyl, isopropyl, methoxy, halide, cyano, nitro, sulfonamido, amino, dimethylamino, carboxy, dicarboxy, di(methoxycarbonyl) and di(hydroxymethyl).

7. A compound according to claim 1, wherein $R^1$ is selected from the group consisting of hydrogen, 2-aminoethyl, 3-aminopropyl, 2-(1-pyrrolidinyl)ethyl, 3-(1-pyrrolidinyl)propyl, 2-hydroxyethyl and 3-hydroxypropyl.

8. A compound according to claim 1, wherein $OR^6$ is selected from the group consisting of hydroxy, 2-aminoethoxy, 3-aminopropoxy, 2-dimethylaminoethoxy, 3-dimethylaminopropoxy, 3-amino-2-hydroxypropoxy, 2,3-diaminopropoxy, 2-(1-pyrrolidinyl)ethoxy and 3-(1-pyrrolidinyl)propoxy.

* * * * *